United States Patent [19]

Gessman

[11] Patent Number: 5,321,618
[45] Date of Patent: Jun. 14, 1994

[54] APPARATUS AND METHOD FOR REMOTELY MONITORING IMPLANTED CARDIOVERTER DEFIBRILLATORS

[76] Inventor: Lawrence Gessman, 1929 West Point Ct., Cherry Hill, N.J. 08003

[21] Appl. No.: 53,852

[22] Filed: Apr. 27, 1993

Related U.S. Application Data

[63] Continuation of Ser. No. 529,916, May 29, 1990, abandoned.

[51] Int. Cl.$^5$ ............................ G06F 15/42; A61N 1/36
[52] U.S. Cl. ............................ 364/413.06; 364/413.02; 364/413.03; 364/413.04; 379/38; 379/105; 379/106; 128/696; 128/700
[58] Field of Search ............ 364/413.02, 413.06, 364/413.03, 413.04; 379/38, 105, 106; 128/696, 700

[56] References Cited

U.S. PATENT DOCUMENTS

| | | | |
|---|---|---|---|
| 3,882,277 | 5/1975 | DePedro et al. | 128/2.06 |
| 4,102,332 | 7/1978 | Gessman | 128/700 |
| 4,531,527 | 7/1985 | Reinhold et al. | 128/696 |
| 4,614,192 | 9/1986 | Inram et al. | 128/419 |
| 4,803,625 | 2/1989 | Fu et al. | 364/413.03 |

Primary Examiner—Roy N. Envall, Jr.
Assistant Examiner—Gita D. Shingala
Attorney, Agent, or Firm—William H. Murray

[57] ABSTRACT

An apparatus for remotely monitoring the performance of an implanted cardioverter defibrillator includes a remote apparatus adapted which receives commands from and transmits data to a central monitoring facility over telephone communication channels. The remote apparatus includes equipment for acquiring a patient's ecg waveform and transmitting that waveform to the central facility over the telephone communication channel. The remote apparatus also includes a segment, responsive to a command received from the central monitoring facility, for enabling the emission of audio tone signals from the cardioverter defibrillator. These audio tones are detected and sent to the central monitoring facility via the telephone communication channel. The remote apparatus also includes patient alert devices which are activated by commands received from the central monitoring facility over the telephone communication channel.

12 Claims, 6 Drawing Sheets

APPARATUS AND METHOD FOR REMOTELY MONITORING IMPLANTED CARDIOVERTER DEFIBRILLATORS

This is a continuation of copending application Ser. No. 07/529,916 filed on May 29, 1990, now abandoned.

BACKGROUND OF THE INVENTION

This invention relates to methods and apparatus for remotely monitoring the performance of medical electronic devices and more particularly an apparatus and method for remotely monitoring the performance of an implanted cardioverter defibrillator.

An implanted defibrillator is a pacemaker-like device that senses intrinsic cardiac rhythm. If the device determines that a rapid, life threatening ventricular tachycardia or ventricular fibrillation is present, a battery within the device charges a large capacitor, and then discharges the capacitor to deliver a defibrillatory shock to the patient for the purpose of returning the heart to normal rhythm.

One such device is known as an automatic implanted cardioverter defibrillator (AICD) and is manufactured by Cardiac Pacemakers Inc., St. Paul, Minn. This device determines the presence of ventricular tachycardia or ventricular fibrillation by using programmable rate criteria. That is, a detected rate greater than 150, 160, 170, etc. will be classified as ventricular tachycardia or ventricular fibrillation. This device is connected to the heart via four electrodes, two of which are similar to pacemaker electrodes. The device attempts to sense the patients ecg via these electrodes, thereby determining the heart rate. The other two electrodes are used to deliver the defibrillatory shock.

The proper sensing by the device is monitored by obtaining a "beep-o-gram". When a magnet is placed over the device, it will admit a 3200 Hz, 50–100 msec duration audible beep in response to every ecg QRS complex sensed. The monitoring physician performs a beep-o-gram by connecting the patient to a surface ecg; and, while watching the ecg, listening for a beep coincident with the observation of each QRS complex. The beep can be simultaneously recorded on a two channel chart recorder with the surface ecg to visually display and make permanent records of the beep-o-gram. Additional information concerning beep-o-grams may be found in the paper entitled "The Use of Beep-O-Grams In the Assessment of Automatic Implantable Cardioverter Defibrillator Sensing Function", Ballas, S. L., et al., PACE, Volume 12, pages 1737–1745, November, 1989, which paper is incorporated by reference as if fully set forth herein.

Oversensing can be determined if more than one beep is present per QRS complex, or if a beep occurs with each QRS and T wave. Oversensing of this type, called double sensing, would fool the device into thinking that the heart rate was twice what it really is, causing inadvertent shocks if the patients heart rate was more than 75–90 beeps per minute.

Undersensing can be determined if no, or intermittent beeps are heart coincident with QRS complex. Such might be due to a loose electrode, poor electrode contact, high electrode impedance or device malfunction. In any case, undersensing can cause the device to miss the episode of ventricular tachycardia or ventricular fibrillation, thereby denying the patient defibrillatory therapy when it is needed.

The current generation of implanted cardioverter defibrillators can be turned off by applying a magnet over the device for greater than 30 seconds but less than 60 seconds. Thus, in order to obtain a beep-o-gram, the magnet must be applied to the device for less than 30 seconds to avoid shutting the device off.

Pacemaker patients are routinely followed conveniently at home by issuing them telephone ecg transmitters. The device connects to the patient by two electrodes, amplifies the ecg, converts the ecg via voltage to frequency modulation centered at 1500–2000 Hz for telephone transmission. A frequency to voltage demodulator in the pacemaker follow up company location is used to demodulate the ecg for display to a monitor technician or physician.

Pacemakers remain inhibited if the patients intrinsic heart rate is greater than the pacer's programmed rate. Pacemakers pace the heart, displaying a pacing artifact in front of every paced QRS complex on the surface ecg, if the patients heart rate falls below the pacemakers programmed escape pacing rate. Thus, proper sensing can be determined by seeing that the device does not pace when the patients heart rate is adequate, and does pace when not adequate. To expedite the telephone monitoring, a magnet placed over the pacer will cause it to pace even if heart rate is adequate, thereby enabling determination of pacemaker capture. Capture is defined as whether the output of the pacer is sufficient to pace the heart, which is determined by seeing a QRS complex initiated and following every pacing artifact.

SUMMARY OF THE INVENTION

Although the beep-o-gram provides the physician with an effective tool for monitoring the operation of the device, such beep-o-gram must at present be obtained in the doctor's office. This severely limits the utility of the beep-o-grams since substantially all of the shocks initiated by the implanted device being monitored will occur outside of the physician's presence. Consequently, it is not now possible for a patient to have the sensing function of their implanted device, and their ecg rhythm determined immediately post-receiving a shock unless such shock happened to take place at the time the patient was in the physician's office where a post-shock beep-o-gram could be initiated promptly.

Such prompt determination of the sensing function and ecg rhythm is important to enable the physician to determine whether the shock was appropriate (that is, due to a presumed arrhythmia), or inappropriate (that is, not due to arrhythmia, but rather mis-sensing or device malfunction). It has been estimated that one third of current outpatient shock episodes are due to mis-sensing, or shocking the wrong arrhythmia. Other arrhythmia, besides ventricular tachycardia and ventricular fibrillation, can occur that exceed the device heart rate criteria, but ideally should not be shocked. These arrhythmia, if found to be present at that time of shock, can substantially be suppressed by adding appropriate anti-arrhythmia medication.

Although monitoring after a shock does not tell the monitoring physician what caused the shock, the reason can be inferred. For example, if a person faints, or feels palpitation and nearly faints immediately before receiving a shock, and the arrhythmia can be inferred to be ventricular tachycardia or ventricular fibrillation. If the patient does not feel palpitations associated with nearly fainting before shock, the shock may have due to a non-life threatening arrhythmia, such as atrial fibrillation, or inadvertent mis-sensing.

It is therefore an object of the present invention to provide an apparatus and method for remotely monitoring implanted cardioverter defibrillators.

It is another object of the present invention to provide an apparatus and method for remotely monitoring implanted cardioverter defibrillators using telephone communication channels.

It is still another object of the present invention to provide an apparatus and method for remotely monitoring an implanted cardioverter defibrillator which provides a hard copy, permanent record of the monitored functions.

It is a further object of the present invention to provide an apparatus and method for remotely monitoring implanted cardioverter defibrillators in which the operation of the implanted defibrillator is controlled by an operator at the remote location and not by the patient thereby substantially reducing the possibility of patient induced malfunctions.

The present invention enables a physician or technician at a central facility to monitor the operation of the defribrillator while the patient is present in a location remote to the central monitoring facility. The central monitoring facility comprises telephone communication means for transmitting commands to a receiving data from a remote monitoring apparatus present at the patient's location. The central facility also includes means for receiving patient electrocardiogram signal data from the telephone communication means and displaying this data on one channel of a two-channel recorder. The central facility also includes means for generating a command to the remote apparatus through the telephone communication means for enabling emission from the cardioverter defibrillator of audio tone signals coincident with sensed events. In addition, the central facility includes means for receiving the audio tone signals from the telephone communication means and displaying them on the other channel of the two-channel recorder.

The remote apparatus comprises telephone communication means for receiving commands from and transmitting data to the central monitoring facility over telephone communication channels. Also included are means for acquiring patient electrocardiogram signals and coupling the signals to the telephone communication means for transmission to the central monitoring facility. The remote apparatus also includes means, responsive to a command received from the central monitoring facility, for enabling the emission of the audio tone signals from the cardioverter defibrillator; and means for detecting the audio tone signals and coupling the same to the telephone communication means for transmission to the central monitoring facility.

BRIEF DESCRIPTION OF THE DRAWINGS

The foregoing and further features of the invention are shown on the accompanied drawing in which.

DETAILED DESCRIPTION

Figure 1:
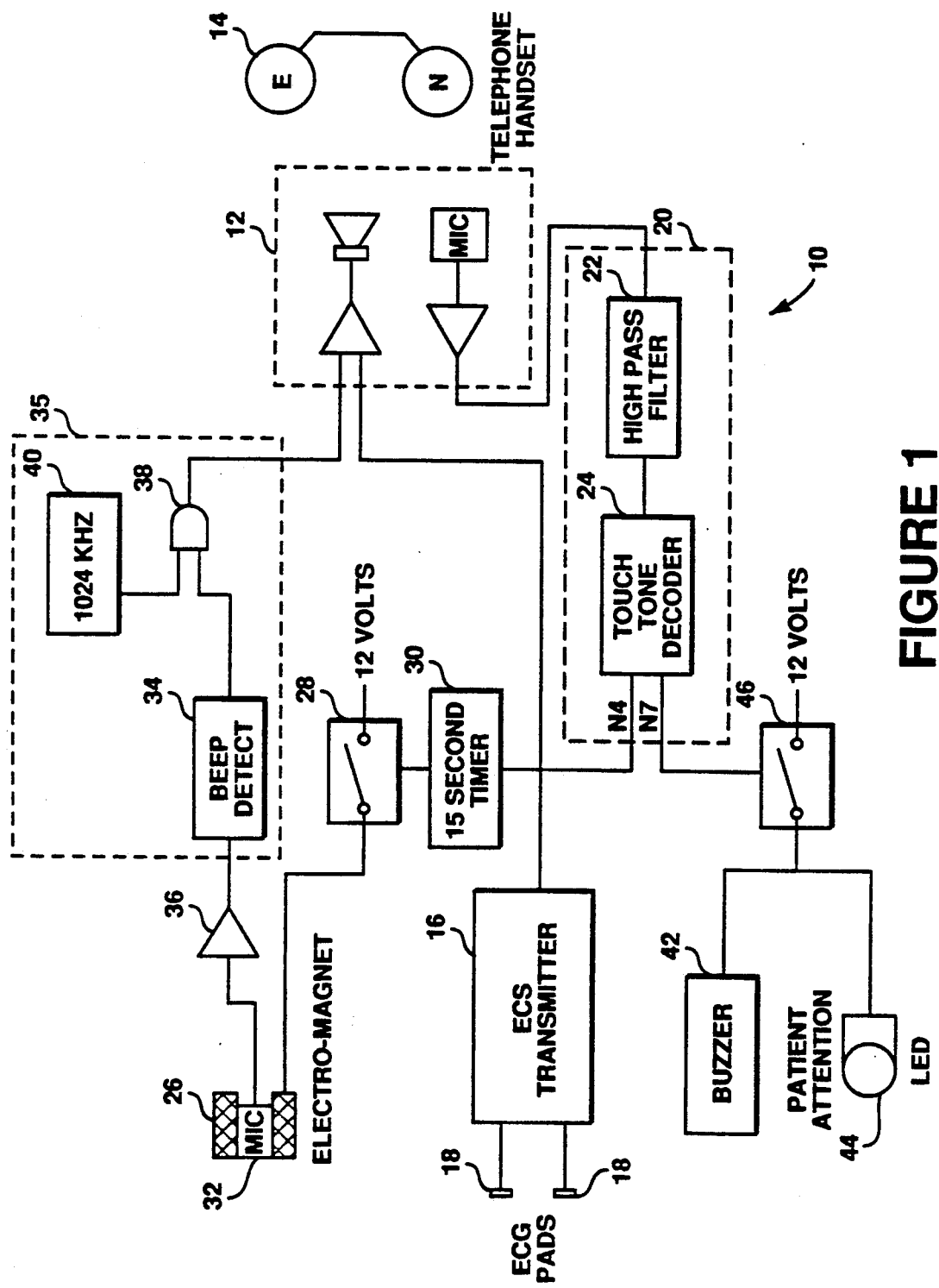
FIG. 1 is a block diagram of a preferred embodiment of a remote apparatus for monitoring implanted cardioverter defibrillators in accordance with the present invention.

Referring now to FIG. 1 there is shown a block diagram of a preferred embodiment of a remote unit, generally designated 10. The remote 10 includes an acoustic coupler 12 for receiving commands from and transmitting data to a central monitoring facility 100 (see FIG. 2) through a telephone handset 14 over telephone communication channels. It should be noted that the telephone handset 14 is part of the patients telephone receiver and is not part of the preferred embodiment of the remote unit 10. A direct connection to the telephone line, or a radio or cellular telephone connection could also be used.

The remote unit 10 also includes an ecg transmitter 16. The ecg transmitter 16 includes a set of ecg pads 18 which are secured to the patient as is known in the art of electrocardiograms. Finger electrodes could also be used. The FM modulated output of the ecg transmitter 16 is a signal comprising the patient's ecg waveform and is coupled to the acoustic coupler 12 for transmission to the central facility 100 (see FIG. 2) over telephone communication channels by means of the telephone handset 14.

The remote unit 10 also includes a function controller 20 for generating function control signals in response to commands received from the central facility over the telephone communication lines through the telephone handset 14 and acoustic coupler 12. The function controller 20 basically decodes touch tone commands received from the central facility. The controller 20 includes a high pass filter 22 connected between the acoustic coupler 12 and a touch tone decoder 24. The touch tone decoder 24 produces an output signal based upon a specific combination of touch tone input signals. For example, the touch tone decoder 24 will produce an output signal on line *4 upon receipt of touch tone signals corresponding to *4 and an output signal on line *7 upon receipt of touch tone signals corresponding to *7.

The remote unit 10 also includes an electromagnet assembly 26. The electromagnet assembly 26 is functionally compatible with the implanted cardioverter defibrillator such that when the electromagnet assembly 26 is placed in proximity to the implanted defibrillator, energization of the electromagnet for a predetermined period of time will cause the implanted cardioverter defibrillator to admit audible tones as previously described. In the preferred embodiment, the electromagnet 26 has a strength of approximately 120 gauss. The electromagnet 26 is electrically connected to a 12 volt power source through a first relay switch 28. The opening and closing of the first switch 28 is controlled by a signal applied to a control input.

The *4 signal output from the touch tone decoder 24 is coupled to the input of a 15 second timer 30. The output of the 15 second timer 30, which is signal which remains for 15 seconds following the application of the input signal to the timer, is coupled to the control input of the first switch 28. Consequently, a *4 signal from the touch tone decoder 24 will cause the first switch 28 to close for 15 seconds thereby applying 12 volt power to the electromagnet 26 for 15 seconds.

The remote unit 10 also includes a microphone 32. The microphone 32 is compatible with the implanted cardioverter defibrillator in that it will pick up the audible tones, or beeps admitted by the defibrillator upon activation of the electromagnet 26. The output of the microphone 32 is coupled to a beep detector 34 through an amplifier 36. The beep detector 34 contains a tuned filter that passes the 3200 Hz beep tones, but excludes higher or lower frequencies and provides an output signal upon detection of a beep of the cardioverter defibrillator sensed by the microphone 32 and applied to the input of the beep detector 34 through the amplifier 36. The output signal will remain for the duration of the detected beep. For example, in the preferred embodiment, the defibrillator admits a 3200 Hz, 50-100 msec duration audible beep; accordingly, the output signal from the beep detector 34 will be a high level logic signal of 50-100 msec duration. This output signal is applied as a gating signal to one input of a two input gate 38.

Figure 5:
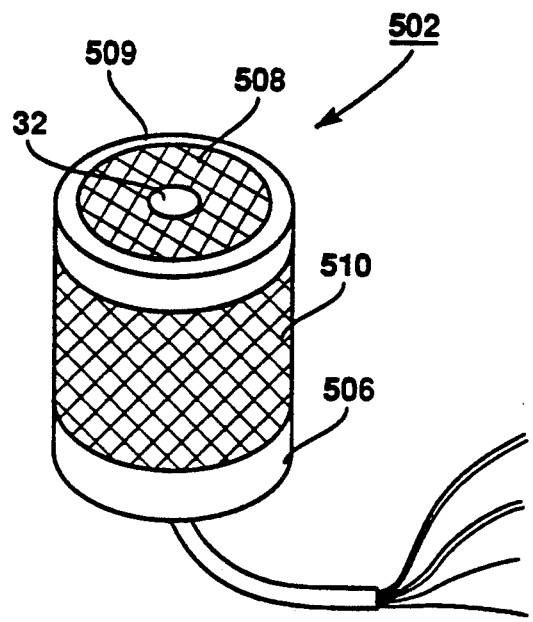
FIG. 5 is an isometric depiction of a hand-held patient module in accordance with the present invention.

In an alternative preferred embodiment of the remote unit 10 of the present invention, the ECG pads 18, the electromagnet 26 and the microphone 32 are integrated into a hand-held patient module 502 as depicted, for example, in FIG. 5. The patient module 502 is substantially cylindrical in shape, having a substantially planar bottom portion 504 and a cylindrical wall 506. Electrical conductive material, such as a conductive velcro mesh, is disposed on the bottom surface 504 of the patient module 502. This will form an ecg contact 508 which the patient will place in contact with his body proximate to the implanted defibrillator as will be subsequently described. Electrical conductive material, for example, conductive velcro mesh, is disposed about the cylindrical wall 506 and forms a second ecg electrode 510. The second ecg electrode 510 is electrically insulated from the first ecg electrode 508. The second ecg electrode 510 will come into electrical contact with the fingers of the right hand of the patient. Accordingly, when the patient grasps the module 502 with the fingers of his right hand contacting the electrode 510 and places the module 502 in contact with the left upper quadrant of his abdomen proximate to the implanted defibrillator, the electrodes 508 and 510 will form a lead 2 equivalent ecg; that is, RA to left leg.

Figure 6:
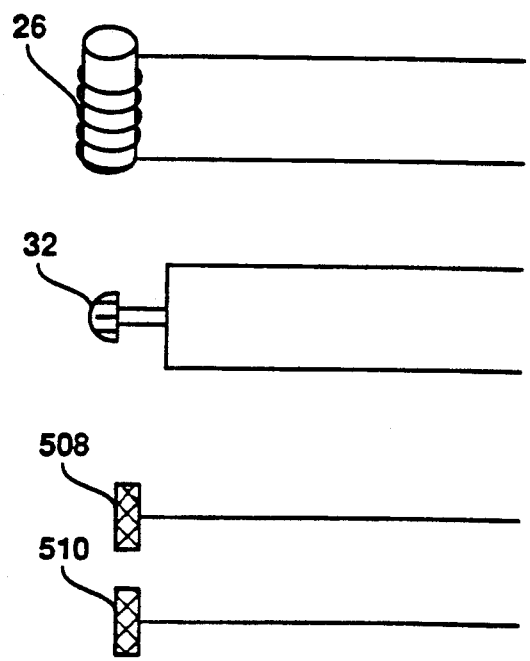
FIG. 6 is a schematic representation of the components which are included within the hand-held patient module depicted in FIG. 5.

In addition to the lead 2 equivalent ecg electrodes, the module 502 incorporates the microphone 32 and can sense beeps from the implanted defibrillator through an aperture in the bottom portion 504 of the module 502. In addition, the electromagnet 26 is also disposed in the module 502 in proximity to the bottom surface of 504 so that when the patient places the bottom surface 504 in proximity to the implanted defibrillator, activation of the electromagnet 26 will cause the defibrillator to emit the beep tones which will be picked up by the microphone 32 for transmission back to the central facility. At the same time, the patient's ecg waveform will be picked up through the lead 2 equivalent ecg electrodes 508 and 510 by virtue of the fact that the electrode 508 is in contact with the patient's skin in proximity to the implanted defibrillator and electrode 510 is in contact with the fingers of the patient's right hand. FIG. 6 depicts, schematically, the components and associated wiring of the module 502.

Figure 3:
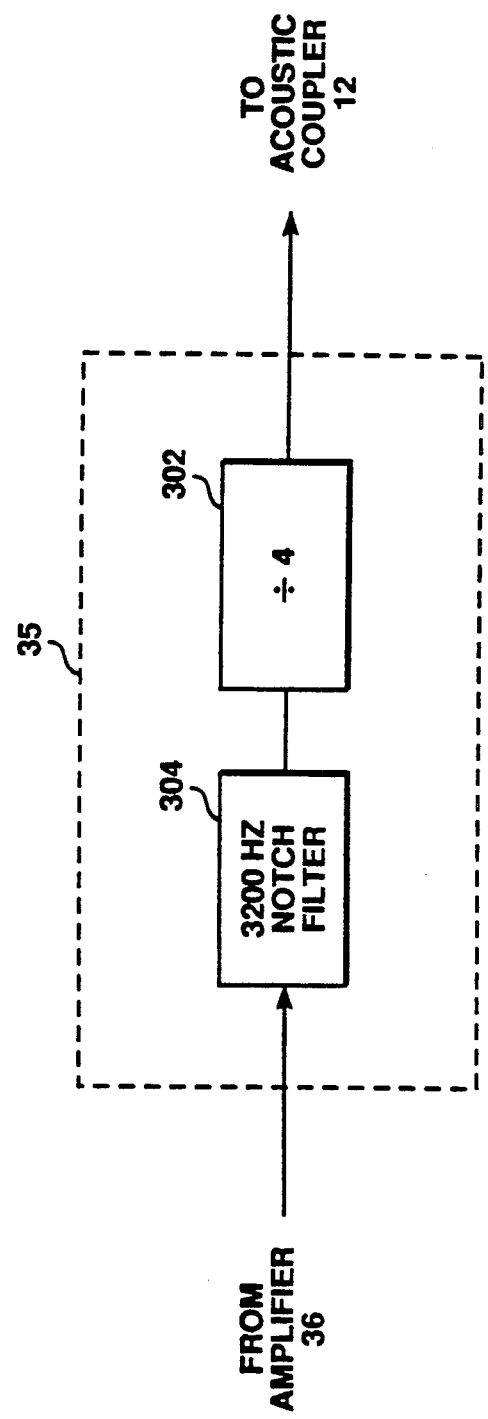
FIG. 3 is a block diagram of an alternate preferred embodiment of a beep detector portion of the remote apparatus depicted in FIG. 1.

The remote unit 10 also includes a 1024 KHz signal generator 40. The output of the signal generator 40 is an AC signal having a frequency substantially equal to 1024 KHz and is coupled to the second input of the two input gate 38. The output of the two input gate 38 is a signal which appears upon coincidence of the signals at the two input. In the preferred embodiment depicted, the output of gate 38 will comprise an AC signal having a frequency of 1024 KHz and a duration of 50-100 msec when an output signal is generated by the beep detector 34. The output of gate 38 will correspond to the audible tone or beep admitted by the cardioverter defibrillator except that it will have a frequency of 1024 KHz instead of 3200 Hz in order to avoid interference with the frequency of signals involved in telephone communications, to avoid interference from the FM modulated ecg (center frequency 1700-2000 Hz) and to be within the band pass of the telephone line (500-2600 Hz). The output of the gate 38 is coupled to the input of the input coupler 12. Alternately, beep detector 34 could simply be a frequency divide by four circuit 302 (see FIG. 3) converting the 3200 Hz beep tone to an 800 Hz tone to present directly to the acoustic coupler 12 thereby eliminating the signal generator 40 and the gate 38. In this alternate embodiment, the divide by four circuit 302 is preceded by a 3200 Hz notch filter 304; and the components depicted in FIG. 3 replace those shown within dashed line 35 in FIG. 1.

The remote unit 10 also includes a patient audio alert device such as a buzzer 42 and a patient video alert device such as a light emitting diode (LED) 44. The buzzer 42 and LED 44 are selectively activated by means of the second switch 46. Upon receipt of a signal at its control input, the second switch 46 will close thereby applying the 12 volt electrical power to the buzzer 42 and LED 44. The *7 output of the touch tone decoder 24 is coupled to the control input of the second switch 46. This is used to alert the patient to pick up his telephone handset to talk to the central facility operator.

Figure 2:
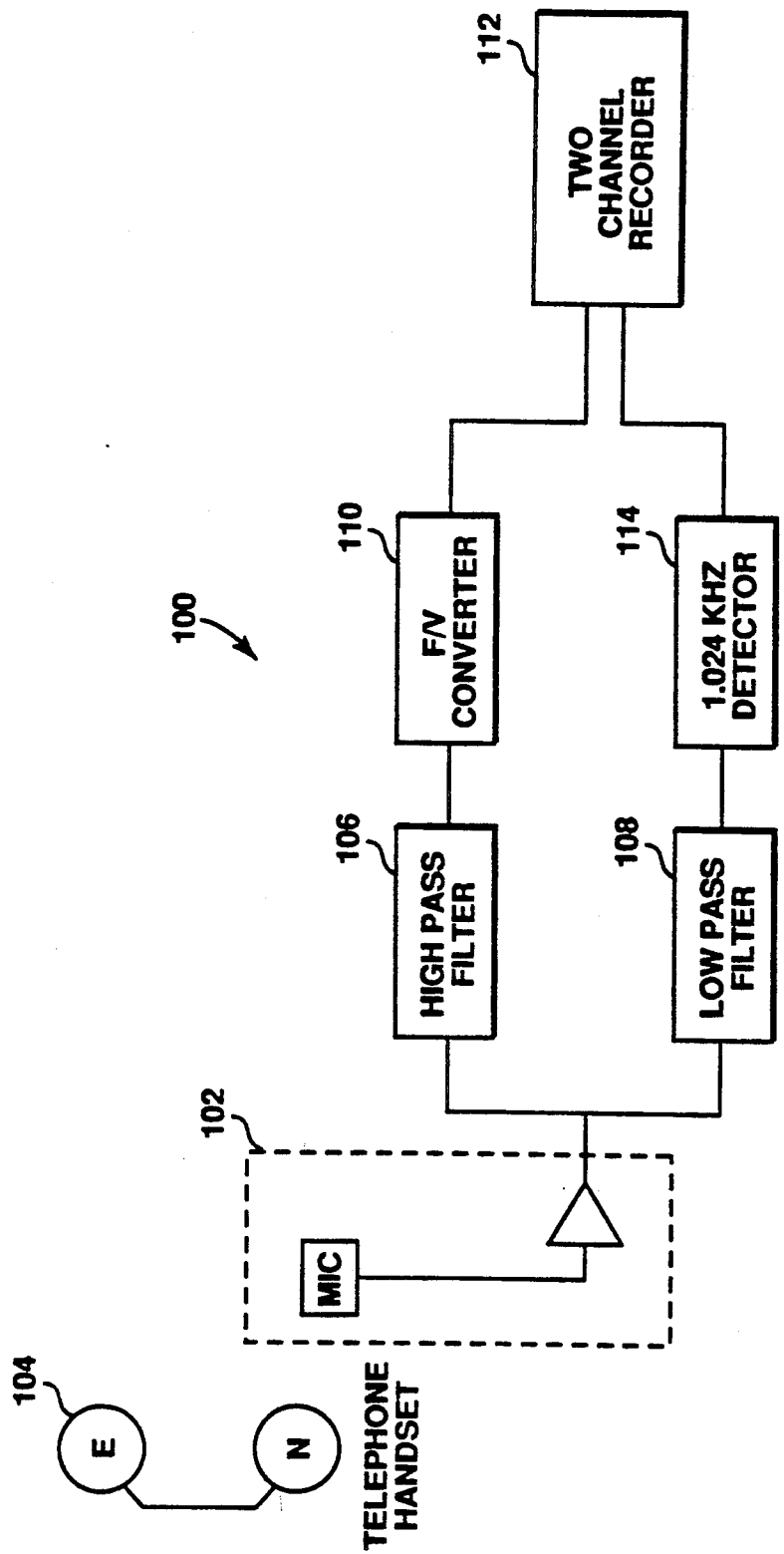
FIG. 2 is a block diagram of a preferred embodiment of a central facility for use in connection with the remote apparatus depicted in FIG. 1.

Referring now to FIG. 2, there is shown a block diagram of a preferred embodiment of a central facility generally designated 100. The central facility 100 includes an acoustic coupler 102 for use in connection with a telephone handset 104. The acoustic coupler 102 includes a microphone for receiving signals from the remote unit 10 over the telephone communication lines. A direct connection to the telephone line could also be used. The output from the microphone of the acoustic coupler 102 is coupled to a high pass filter 106 and a low pass filter 108. The high pass filter 106 will filter out those signals relating to the 1024 KHz pulses (or 800 Hz pulses if the divide by four circuit is used) while passing those signals relating to the FM modulated electrocardiogram. Similarly, low pass filter will filter out those signals relating to the electrocardiogram while passing those signals relating to the 1024 KHz (or 800 Hz) pulses. The output of the high pass filter 106 is coupled to the input of a frequency to voltage converter 110. The frequency to voltage converter 110 demodulates the frequency modulated electrocardiogram signal. The output of the frequency to voltage converter 110, which is the electrocardiogram signal as recorded by the remote unit 10, is coupled to one channel of a two-channel recorder 112.

The output of the low pass filter 108 is coupled to the input of a 1024 KHz (or 800 Hz) detector 114. The detector 114 will provide an output signal upon detection of a 1024 KHz (or 800 Hz) signal at its input. The duration of the output signal is commensurate with the duration of the input 1024 KHz (or 800 Hz) signal. Accordingly, the output signal from the detector 114 is substantially equal to a series of pulses representative of the audible tones or beeps emitted by the cardioverter defibrillator which were sensed by the microphone 32 of the remote unit 10. The output of the detector 114 is coupled to the second channel of the two-channel recorder 12.

The apparatus for remotely monitoring an implanted cardioverter defibrillator operates as follows. Telephone contact can be initiated by either the patient or by the central station depending upon the monitoring circumstances. For example, if a patient has just experienced a shock episode, the patient may want to initiate telephone contact in order to determine the circumstances under which the shocking has occurred. On the other hand, the central facility may want to initiate telephone contact as a result of routine monitoring procedures which have been prescheduled.

Figure 4:
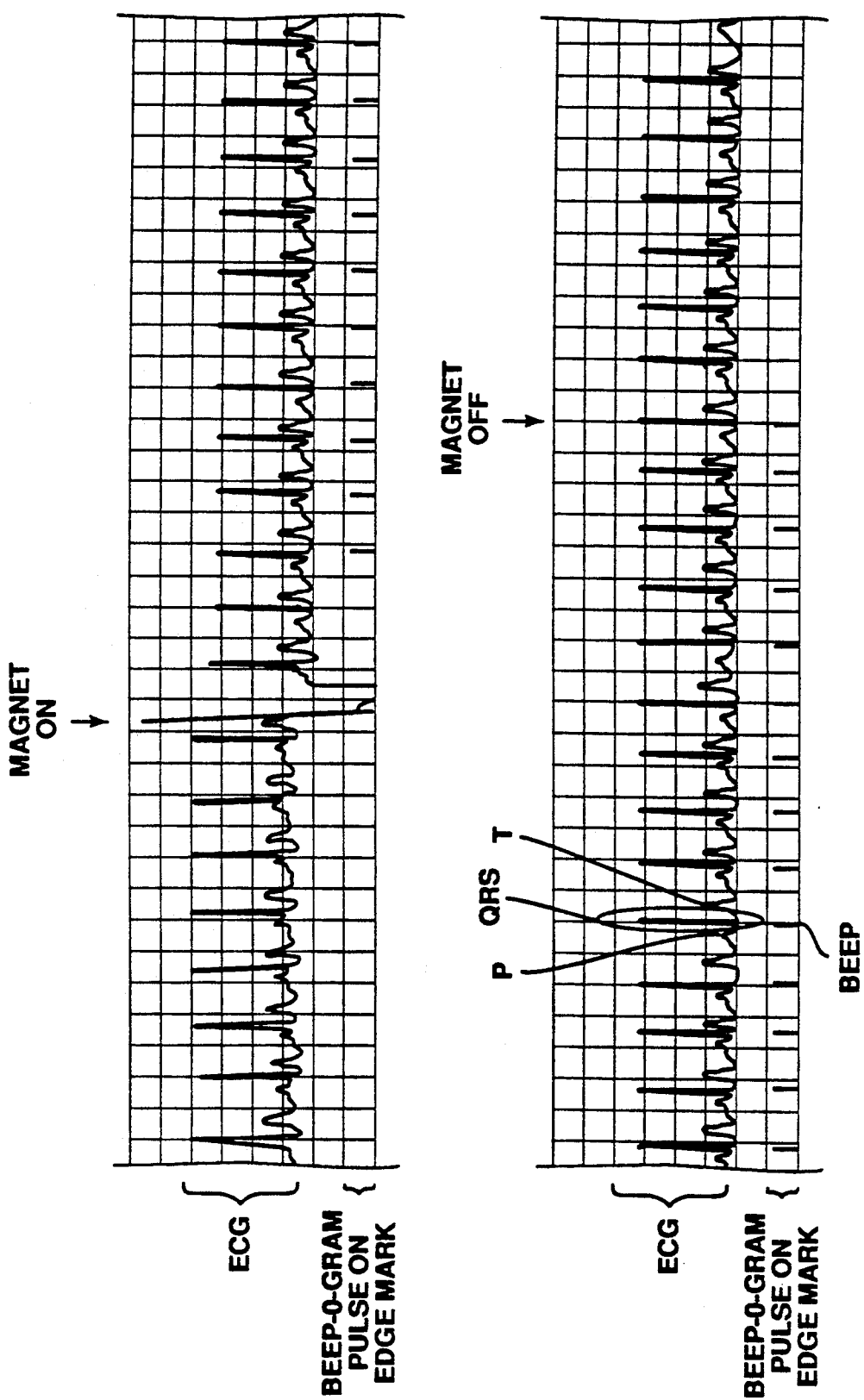
FIG. 4 is a depiction of a chart recording of an ecg waveform on one channel and a series of beep pulses on a second channel.

After telephone contact has been made, the attendant or physician at the central station can verbally instruct the patient to put on the pasted-on ecg monitor pads or finger connect contacts and to connect them to the ecg transmitter connections in the remote unit 10. The patient will then be instructed to placed the telephone handset into the acoustic coupler cradle on the remote unit and wait for the activation of the patient alert signals, either the buzzer 42 and/or the LED 44. Activation of the buzzer 42 and/or LED 44 will alert the patient to then hold the electromagnet 26/microphone 32 assembly over the implanted defibrillator. The attendant then uses his telephone touch tone dial to send a *4 sequence which will turn on the electromagnet for 15 seconds. The resulting timing beeps are detected by the microphone in the electromagnet 26/microphone 32 assembly and converted to 1024 Hz (or 800 Hz if the divide by four circuit is used) tone bursts which are then transmitted to the central facility over the telephone lines. The two-channel recorder in the central facility 100 will then display both the ecg waveform from the patient along with a series of beep timing pulses for the duration of the 15 second electromagnet turn-on as shown, for example, in FIG. 4. As depicted in FIG. 4, there is a beep pulse associated with each QRS waveform of the ecg. These beeps begin following the point at which the magnet is turned on and they stop following the point at which the magnet is turned off.

Figure 7:
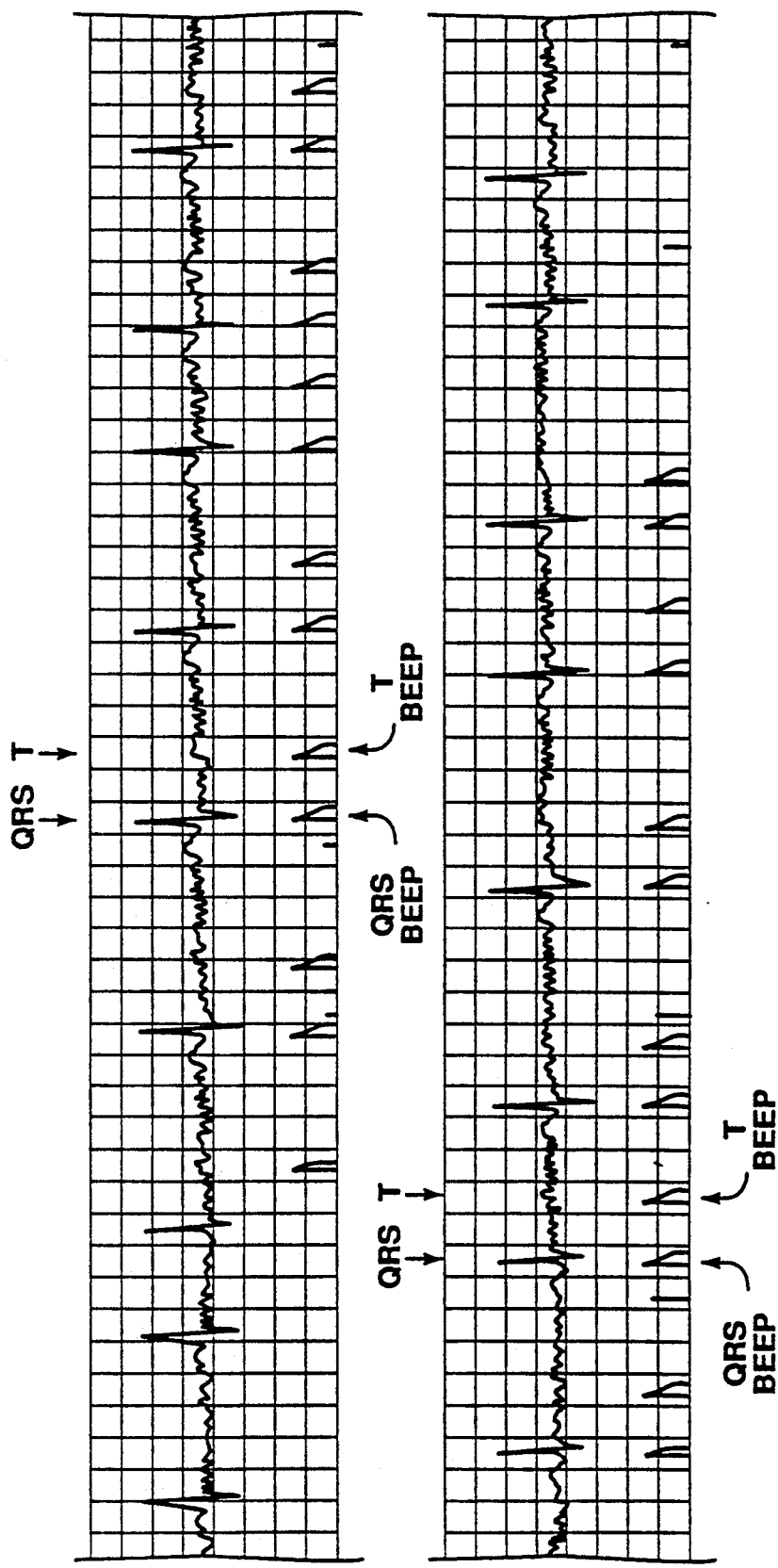
FIG. 7 is a depiction of a chart recording of an ecg waveform on one channel and a series of beep pulses on a second channel and further depicting an abnormality in the defibrillator whereby a beep is produced by a T wave as well as by a QRS wave.

FIG. 7 depicts an ecg waveform and corresponding beep timing pulses which reflect an abnormality in the monitored defibrillator. As can be seen in FIG. 7, there is a beep pulse associated with each T waveform of the ecg as well as a beep pulse associated with each QRS waveform. This illustrates a double-sensing situation in which the defibrillator has erroneously sensed the T wave in addition to the QRS complex. Such over-sensing, or double-sensing, could fool the implanted defibrillator into thinking that the heart rate was twice what it really is, causing inadvertent shocks if the heart rate was more than the predetermined limit.

Once the display is completed and recorded, the attendant then uses his telephone touch tone dial to send a *7 sequence to once again activate the buzzer 42 and LED 44 patient alerts. Activation of these alerts signals the patient to pick up the telephone handset and listen to any further instructions which may be given by the central facility attendant.

Although telephonic communication between the remote and central units is facilitated by acoustic couplers in the preferred embodiment described herein, such may also be facilitated by direct wire interface and cellular techniques and such are considered to be within the scope of the present invention.

It should be noted that the fifteen second, touch tone controlled electromagnet is an important feature of the invention. Patient home use of an ordinary magnet, which is commonly done in ordinary pacemaker follow-ups, could cause inadvertent "turning off" of the implanted defibrillator if a greater than thirty second magnet application was inadvertently performed by the patient. This safety feature will allow physician's acceptance of the device.

As can be seen from the above description, of the present invention enables the monitoring of the implanted defibrillator shortly after the onset of a shocking episode. This is possible since the patient simply initiates telephone contact with the central facility which then performs the monitoring function over the telephone communication lines without the necessity of having the patient actually come to the monitoring facility. Such is not only convenient for the patient, it provides better information on the operation of the implanted defibrillator since the monitoring function will occur so close to the onset of a shocking episode.

It will be understood that various changes in the details, materials and arrangement of the parts which have been described and illustrated in order to explain the nature of this invention may be made by those skilled in the art without departing from the principles and scope of the invention as expressed in the following claims.

I claim:

1. An apparatus for remotely interrogating and monitoring the operation of a cardioverter defibrillator of the type which emits, upon enablement, audio tone signals coincident with sensed events, said apparatus comprising:
    a) telephone communication means for receiving differing commands from a central monitoring facility by way of a telephone communication channel thereby providing differing telephone received commands and transmitting data to said central monitoring facility by way of said telephone communication channel;
    b) means for acquiring differing patient electrocardiogram signals and coupling same to said telephone communication means for transmission to said central monitoring facility;
    c) detector means, responsive to said differing telephone received commands received from said central monitoring facility by way of said telephone channel, for selectively enabling the emission of said audio tone signals wherein said audio tone signals are representative of selected electrocardiogram signals of said acquired electrocardiogram signals thereby providing said remote interrogating and monitoring of said cardioverter defibrillator by said central monitoring facility; and, d) means for detecting said audio tone signals and coupling same to said telephone communication means for transmission to said central monitoring facility.

2. The apparatus in accordance with claim 1 wherein said means for enabling the emission of audio tone signals comprises means for remotely controlling the energization of an electromagnet for a predetermined period of time.

3. The apparatus in accordance with claim 2 wherein said predetermined period of time is 10 to 25 seconds.

4. The apparatus in accordance with claim 1 wherein said means for detecting said audio tone signals and coupling same to said telephone communication means for transmission to said central monitoring facility comprises means for remodulating the tones within a predetermined frequency band pass.

5. The apparatus in accordance with claim 4 wherein said frequency band pass comprises 500–2600 Hz.

6. The apparatus in accordance with claim 1 wherein the means for detecting said audio tone signals and coupling same to said telephone communication means for transmission to said central monitoring facility comprises means for reencoding the tones within a predetermined frequency band pass.

7. The apparatus in accordance with claim 6 wherein said frequency band pass comprises 500–2600 Hz.

8. The apparatus in accordance with claim 1, wherein said detector means further comprises means for selectively enabling the emission of a plurality of differing audio tone signals representative of a plurality of differing patient electrocardiogram signals in accordance with said telephone received commands.

9. The apparatus in accordance with claim 1, further comprising means for alerting said patient in response to said telephone received commands.

10. A method for remotely interrogating monitoring the operation of a cardioverter defibrillator of the type which emits, upon enablement, audio tone signals coincident with sensed events, said method comprising:

a) providing telephone communication means for receiving differing commands from a central monitoring facility by way of a telephone communication channel thereby providing differing telephone received commands and transmitting data to said central monitoring facility by way of said telephone communication channel;

b) acquiring patient differing electrocardiogram signals and coupling same to said telephone communication means for transmission to said central monitoring facility;

c) selectively enabling, responsive to said differing telephone received commands received from said central monitoring facility by way of said telephone channel, the emission of said audio tone signals wherein said audio tone signals are representative of said electrocardiogram signals of said acquired electrocardiogram signals thereby providing said remote interrogating and monitoring of said cardioverter defibrillator by said central monitoring facility; and, d) coupling said selectively enabled audio tone signals to said telephone communication means for transmission to said central monitoring facility.

11. The method in accordance with claim 10, wherein step (c) further comprises the step of selectively enabling the admission of a plurality of differing audio tone signals representative of a plurality of differing patient electrocardiogram signals in accordance with said telephone received commands.

12. The method in accordance with claim 10, comprising the further step of alerting said patient in response to said telephone received commands.

* * * * *